United States Patent

Coyne

[11] 3,937,220
[45] Feb. 10, 1976

[54] STERILE ASPIRATION CATHETER

[75] Inventor: Nancy Coyne, Jamaica Plain, Mass.

[73] Assignee: International Paper Company, New York, N.Y.

[22] Filed: Mar. 4, 1974

[21] Appl. No.: 447,869

[52] U.S. Cl............................. 128/276; 206/364
[51] Int. Cl.².................................... A61M 1/00
[58] Field of Search........ 128/348, 349 R, 351, 350, 128/214.4, 276, 278, 277, 2 F; 206/363, 364, 361, 367, 368; 32/33

[56] References Cited
UNITED STATES PATENTS

| | | | |
|---|---|---|---|
| 1,120,549 | 12/1914 | Schellberg | 128/349 R |
| 2,937,643 | 5/1960 | Elliot | 128/214.4 |
| 3,050,066 | 8/1962 | Koehn | 206/364 |
| 3,282,114 | 11/1966 | Pell | 206/361 |
| 3,421,509 | 1/1969 | Fiore | 128/349 |
| 3,516,160 | 6/1970 | Leffler | 32/33 |

*Primary Examiner*—Robert W. Michell
*Assistant Examiner*—Henry S. Layton
*Attorney, Agent, or Firm*—Finnegan, Henderson, Farabow, & Garrett

[57] ABSTRACT

A sterile aspiration catheter is disclosed which includes a catheter tube enclosed within a pliable sleeve and which extends beyond the tube end which is inserted in the patient. Preferably, the sleeve is vented at the end remote from the tube insertion end whereby as the sleeve is retracted from the tube insertion end, air within the envelope escapes through the vent.

1 Claim, 2 Drawing Figures

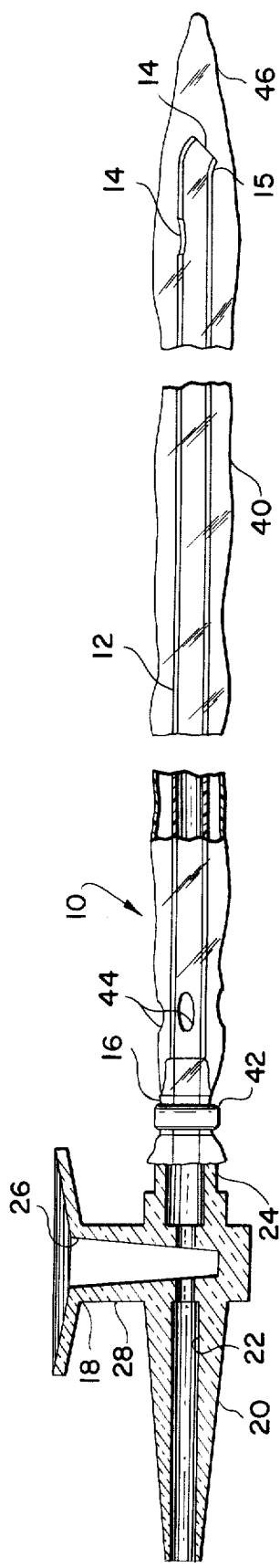
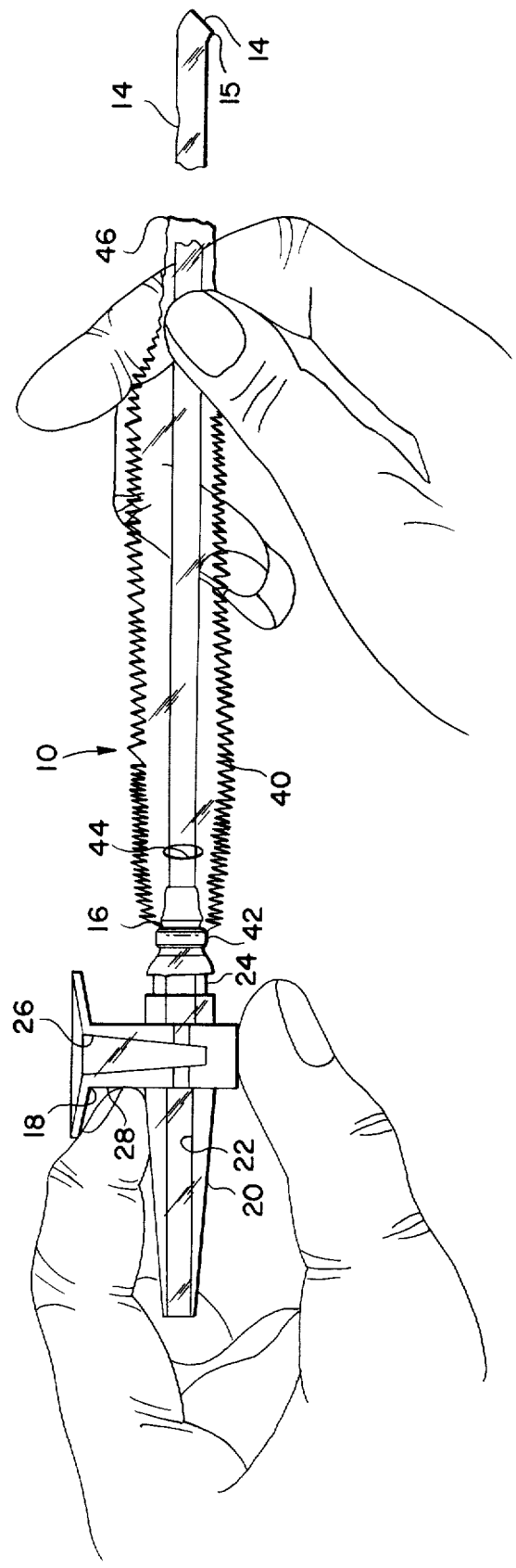
FIG. 1
FIG. 2

STERILE ASPIRATION CATHETER

BACKGROUND OF THE INVENTION

This invention relates to aspiration catheters used for removing fluids from the tracheobronchial passages of patients.

Aspiration, or suction catheters are commonly employed for removing fluids, such as secretions, exudates and blood from the tracheobronchial passages of patients by applying a suction force to the catheter. Suctioning of tracheobronchial passages is performed frequently following a tracheostomy to remove fluids resulting from the surgical procedure. It is essential that the suction catheter be maintained sterile and that effective aseptic technique be used to prevent infection of the patient due to transmission of foreign bacteria into the patient during the suctioning procedure. Effective aseptic procedure includes avoiding contact of the catheter with any foreign object, including the hands of the person inserting the catheter.

In the past, attempts at preventing contamination of the sterile catheter prior to and during use of the catheter included requiring the person performing the suction procedure to wear sterile gloves. However, it is very difficult and time consuming for a person to put these gloves on and use them without their exterior surface touching a foreign object or even the user's hands while the hands are being inserted in the gloves. Any contact of the catheter with a contaminated object will cause the catheter to become contaminated. Therefore, extreme care must be taken to avoid contact of the catheter with any foreign object.

Another problem is cross contamination after the catheter is used as a result of the used catheter carrying infectious secretions. Presently, after a suction catheter is used, it may be rinsed and discarded into a waste receptacle. If the catheter is touched, that person may become infected or become a carrier of the infectious organisms. Consequently, very careful aseptic disposal procedures must be carried out.

Accordingly, it is one objective of this invention to provide an improved suction catheter which avoids contamination prior to and during usage and which minimizes the possibility of cross contamination during disposal of the used catheter.

It is another object of this invention to provide an improved sterile catheter which simplyfies aseptic insertion of the catheter and a method for inserting the catheter into a patient.

Additional objectives and advantages of the invention will be set forth in part in the description which follows, and in part will be obvious from the description, or may be learned by practice of the invention. The objectives and advantages of the invention may be realized and attained by means of the instrumentalities and combinations particularly pointed out in the appended claims.

BRIEF DESCRIPTION OF THE INVENTION

To achieve the foregoing objectives and in accordance with the purpose of the invention, as embodied and broadly described herein, the sterile aspiration catheter of this invention comprises a tube having a fluid flow passageway therethrough and an inlet at one end thereof, the other end of the tube having an outlet adapted to be placed in fluid flow communication with means for effecting fluid flow through the passageway, at least a portion of the tube extending from said inlet toward the outlet adapted for insertion into a patient's tracheobronchial passages, a pliable envelope enclosing at least said portion of the tube and extending beyond the inlet end of the tube, the envelope providing a bacterial barrier, and means for securing the envelope adjacent to the outlet end of the tube.

Preferably the end of the envelope adjacent to the outlet includes vent means for enabling air located within the envelope to escape therethrough as the envelope is moved away from the inlet end.

The invention also comprises a method for inserting into a passage in a patient a catheter having a tube contained within a pliable envelope and means at one end of the tube for effecting fluid flow through the tube, the method comprising the steps of holding the envelope, sliding the first end of the envelope remote from the means toward the means in order to expose a portion of the tube, inserting the exposed portion of the tube into the passage, continuing sliding the first end of the envelope toward the fluid flow effecting means and effecting removal of air from within the envelope through a vent adjacent to the fluid flow effecting means. The invention further includes removing the tube from the patient's passage and sliding the envelope toward the inlet end of the tube to completely cover the inserted portion and disposing of the catheter.

The invention consists in the novel parts, constructions, arrangements, combinations and improvements shown and described. The accompanying drawing, which is incorporated in and constitutes a part of the specification, illustrates one embodiment of the invention and, together with the description, serves to explain the principles of the invention.

BRIEF DESCRIPTION OF THE DRAWING

In the drawing:

FIG. 1 is a side elevational view of a sterile catheter formed in accordance with this invention;

FIG. 2 is a side elevational view of the sterile catheter of FIG. 1 wherein the protective envelope is illustrated in a retracted position with the catheter tube extended for insertion into a patient.

DETAILED DESCRIPTION OF THE INVENTION

Reference will now be made in detail to the present preferred embodiment of the invention, an example of which is illustrated in the accompanying drawing.

In accordance with the invention, a sterile aspirationn catheter is formed of two primary elements, namely a tube and a protective envelope in which the tube is entirely located. As here embodied, a sterile catheter 10 comprises an elongated tube 12 having a passageway 13 therethrough and at least one port 14, and preferably a plurality of ports 14, formed through the tube at the insertion end 15 thereof. The other end 16 of the tube is open and adapted to be mounted on or receive means for effecting fluid flow through the tube 12. For example, the end 16 of the catheter tube 12 may be attached directly or indirectly to a vacuum source (not shown). Preferably, as shown in FIG. 1, the end 16 of the tube 12 is mounted on a fluid flow regulator or suction control 18 which is adapted to be mounted between a vacuum source (not shown) and the catheter tube 12.

The regulator 18 is formed of a longitudinally elongated body 20 having a primary passageway 22 therethrough which is placed in fluid flow communication with the passageway through the tube 12, the tube 12 being frictionally engaged with a tubular extension 24. A bleed passageway 26 transverse to the primary passageway 22 is formed through a transverse extension 28. Flow through the catheter tube 12 is regulated by placing a finger over the bleed passageway 26 in order to control the amount of bleed flow from the atmosphere through the passageway 26 which in turn regulates the flow of fluid through the catheter tube 12. For example, if the passageway 26 is partially covered, the catheter tube 12 will be exposed to only a partial vacuum thereby effecting relatively slow aspiration; whereas if the passageway 26 is completely closed by placing the finger entirely over the passageway 26, the catheter tube 12 will be exposed to the complete vacuum provided by the vacuum source.

In accordance with the invention, in order to maintain the catheter tube 12 in a sterile condition prior to and during usage of the catheter 10, a pliable protective envelope or sleeve 40 having a sufficient length to permit the end 41 of the envelope to extend beyond the distal or insertion end 15 of the catheter tube 12 is placed over the catheter tube 12 thereby completely enveloping the tube. The envelope 40 is attached to the catheter tube 12 remote from the insertion end 15 of the tube by any conventional means, such as a metal or plastic band or clamp 42. The band 42 preferably is placed over the tube at the portion of the tube which is fitted over the regulator extension 24 so that sufficient pressure can be applied onto the envelope by the band 42 without restricting the tube 12 and adversely affecting flow through the tube 12.

At least one, and preferably a plurality of, vent apertures 44 are provided through the envelope 40 at a position remote from the insertion end 15 of the tube 12 or, in other words, adjacent to the regulator 18. The end 46 of the envelope 40 which is adjacent to the insertion end 15 of the tube may be sealed closed but, preferably is unsealed. It is important, however, that if the end 46 is not sealed, that the envelope end 46 extends beyond the tube, such as by approximately one inch so that the envelope completely encases the catheter tube 12 to prevent the catheter tube 12 from contact with any foreign surface. Because of the pliability of the envelope material the end 46 of the envelope beyond the tube 12 will remain closed to prevent airborne contamination even if not sealed.

In order to insert the catheter tube into the appropriate passage of the patient, the physician or nurse grasps the catheter 10 at any point by holding the envelope 40 with the tube 12 inside. If the end 46 of the envelope 40 is sealed, that end must be opened either by cutting it with a scissors or tearing it if the envelope is provided with a weakend tear line (not shown). The insertion end 15 of the catheter tube 12 may then be easily and quickly ejected from the envelope 40 and inserted into the bronchial passageway by manually sliding the end portion 46 of the envelope rearwardly toward the flow regulator 18. During the insertion into the bronchial passageway, the flow regulator bleed passageway is open to prevent suction from being applied to the catheter tube 12. As can be seen in FIG. 2, as the envelope 40 is moved rearwardly it folds into a generally accordian shape since the end adjacent the regulator 18 is restrained from movement by the band 42. The vent apertures 44 permit the air within the envelope to escape from the envelope as the envelope is moved rearwardly thereby preventing entrapment of the air which would form an air pocket within the envelope and could interfere with the rapid and easy retraction of the envelope from the end 15 of the catheter tube 12.

As the catheter tube 12 is withdrawn from the bronchial passageway, the end 46 of the envelope 40 is slipped toward the tube end 15 so that the catheter tube 12 is completely covered prior to disposing of the catheter 10.

The catheter tube may be made of any conventional material normally used for catheters, such as any suitable, flexible plastic or rubber which is not harmful to the patient. The envelope must be pliable and, since catheters of this type are disposable, must also be inexpensive. Therefore a thin, inexpensive, easily workable material is preferred, such as a sheet of 1–1¼ mil polyethylene film which provides a bacterial barrier.

It can be seen from the above description and the accompanying drawing, that this invention provides a sterile catheter which includes a protective envelope for completely protecting the catheter tube prior to and during insertion of the tube into a patient and which minimizes the need for gloves and other extremely careful procedures to avoid contact of the tube with a foreign object to prevent contamination. The invention also permits rapid and easy ejection of the catheter tube from its protective envelope by providing for venting of air trapped within the envelope as the envelope is retracted along the length of the tube. The invention also permits enclosure of the contaminated catheter tube after use to facilitate disposal, thereby providing a more convenient, simple and effective aseptic suction procedure technique with less danger of contamination to both patient and nurse or doctor.

What is claimed is:

1. A sterile catheter comprising a flexible tube having a fluid flow passageway therethrough and a port at one end thereof, a fluid flow regulator in flow communication with said passageway, means to receive a fluid pump to effect fluid flow through said regulator and said passageway, said fluid flow being variable by operation of said regulator, a pliable envelope being attached at its end adjacent to said regulator to one of said one end of said tube and said regulator, the other end of the said envelope extending beyond said one end of said tube and having an opening through which said tube can be ejected, said envelope being freely, slidably retractable along the length of the tube toward said regulator to enable exposure of said tube to an environment outside of said envelope, said envelope having at least one vent hole adjacent to said regulator to enable air within said envelope to escape during retraction of said envelope.

* * * * *